(12) United States Patent
Codrington

(10) Patent No.: US 10,213,672 B2
(45) Date of Patent: Feb. 26, 2019

(54) COMPUTERIZED TRAINING PUNCHING BAG

(71) Applicant: Steven Codrington, Elmont, NY (US)

(72) Inventor: Steven Codrington, Elmont, NY (US)

( * ) Notice: Subject to any disclaimer, the term of this patent is extended or adjusted under 35 U.S.C. 154(b) by 244 days.

(21) Appl. No.: 15/227,902

(22) Filed: Aug. 3, 2016

(65) Prior Publication Data

US 2017/0036087 A1 Feb. 9, 2017

Related U.S. Application Data

(60) Provisional application No. 62/200,554, filed on Aug. 3, 2015, provisional application No. 62/200,792, filed on Aug. 4, 2015.

(51) Int. Cl.
*A63B 69/32* (2006.01)
*A63B 69/20* (2006.01)
(Continued)

(52) U.S. Cl.
CPC .......... *A63B 69/32* (2013.01); *A63B 24/0075* (2013.01); *A63B 69/201* (2013.01); *A63B 71/0622* (2013.01); *G06F 3/147* (2013.01); *G06F 19/3481* (2013.01); *G09B 19/0038* (2013.01); *A63B 21/008* (2013.01); *A63B 21/023* (2013.01); *A63B 71/0054* (2013.01); *A63B 2022/0092* (2013.01); *A63B 2071/063* (2013.01); *A63B 2071/0625* (2013.01);
(Continued)

(58) Field of Classification Search
CPC . A63B 71/06; A63B 71/0619; A63B 71/0622; A63B 71/0669; A63B 2071/0636; A63B 2071/0638; A63B 2071/0647; A63B 2071/065; A63B 2071/0652; A63B 2071/0658; A63B 2071/0675; A63B 2071/0677; A63B 2071/0694; A63B 69/32; A63B 69/201; A63B 24/0075; A63B 2230/06; A63B 2225/62; A63B 2225/093; A63B 2225/20; A63B 2225/50; A63B 2220/833; A63B 2220/56; A63B 2220/53; A63B 2220/17; A63B 2220/806; A63B 2022/0092; A63B 21/008; A63B 21/023; A63B 71/0054; A63B 2071/063; A63B 2071/0625; A63B 2207/02
See application file for complete search history.

(56) References Cited

U.S. PATENT DOCUMENTS 5,941,801 A 8/1999 D'Alto
7,490,941 B2 2/2009 Mintz et al.
(Continued)

OTHER PUBLICATIONS

International Search Report and Written Opinion of the International Searching Authority in PCT/US16/45412, dated Oct. 31, 2016.

*Primary Examiner* — Joshua Lee
(74) *Attorney, Agent, or Firm* — Collard & Roe, P.C.

(57) ABSTRACT

An electronic punching bag includes an elongate bag formed of resilient material, a microprocessor disposed in an interior of the electronic punching bag or at a periphery of the electronic punching bag, and a display screen that extends around more than half of the periphery of the electronic punching bag. The display screen is configured to receive signals from the microprocessor. The signals cause the display screen to display visual signals.

20 Claims, 13 Drawing Sheets

(51) Int. Cl.
- *A63B 71/06* (2006.01)
- *A63B 24/00* (2006.01)
- *G09B 19/00* (2006.01)
- *G06F 19/00* (2018.01)
- *G06F 3/147* (2006.01)
- *A63B 71/00* (2006.01)
- *A63B 21/008* (2006.01)
- *A63B 21/02* (2006.01)
- *A63B 22/00* (2006.01)

(52) U.S. Cl.
CPC ............... *A63B 2071/0652* (2013.01); *A63B 2071/0694* (2013.01); *A63B 2207/02* (2013.01); *A63B 2220/17* (2013.01); *A63B 2220/53* (2013.01); *A63B 2220/56* (2013.01); *A63B 2220/806* (2013.01); *A63B 2220/833* (2013.01); *A63B 2225/093* (2013.01); *A63B 2225/20* (2013.01); *A63B 2225/50* (2013.01); *A63B 2225/62* (2013.01); *A63B 2230/06* (2013.01); *G09G 2300/00* (2013.01); *G09G 2370/16* (2013.01); *G09G 2380/02* (2013.01)

(56) References Cited

U.S. PATENT DOCUMENTS

| | | | |
|---|---|---|---|
| 8,500,453 B2* | 8/2013 | Simon | G09B 5/06 434/322 |
| 9,227,128 B1* | 1/2016 | Carfagna, Jr. | A63B 69/32 |
| 9,511,262 B1* | 12/2016 | DePompe | A63B 24/0075 |
| 2007/0099772 A1 | 5/2007 | Fu et al. | |
| 2007/0187896 A1 | 8/2007 | Moseley | |
| 2008/0215285 A1* | 9/2008 | Bucar | A63B 69/201 702/139 |
| 2009/0048069 A1 | 2/2009 | Sheedy | |
| 2011/0172060 A1* | 7/2011 | Morales | A63B 69/004 482/8 |
| 2011/0223577 A1* | 9/2011 | Simon | G09B 19/003 434/365 |
| 2012/0088222 A1 | 4/2012 | Considine et al. | |
| 2014/0206504 A1 | 7/2014 | Barreras et al. | |
| 2014/0366645 A1 | 12/2014 | Tsai | |
| 2015/0094191 A1* | 4/2015 | Fradin | A63B 24/0062 482/8 |
| 2017/0189731 A1* | 7/2017 | Duncan | A63B 5/22 |

* cited by examiner

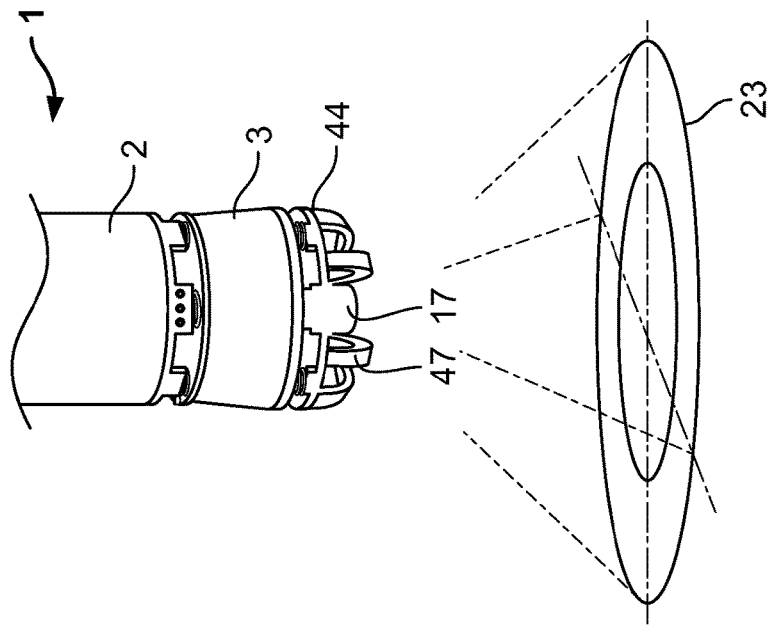
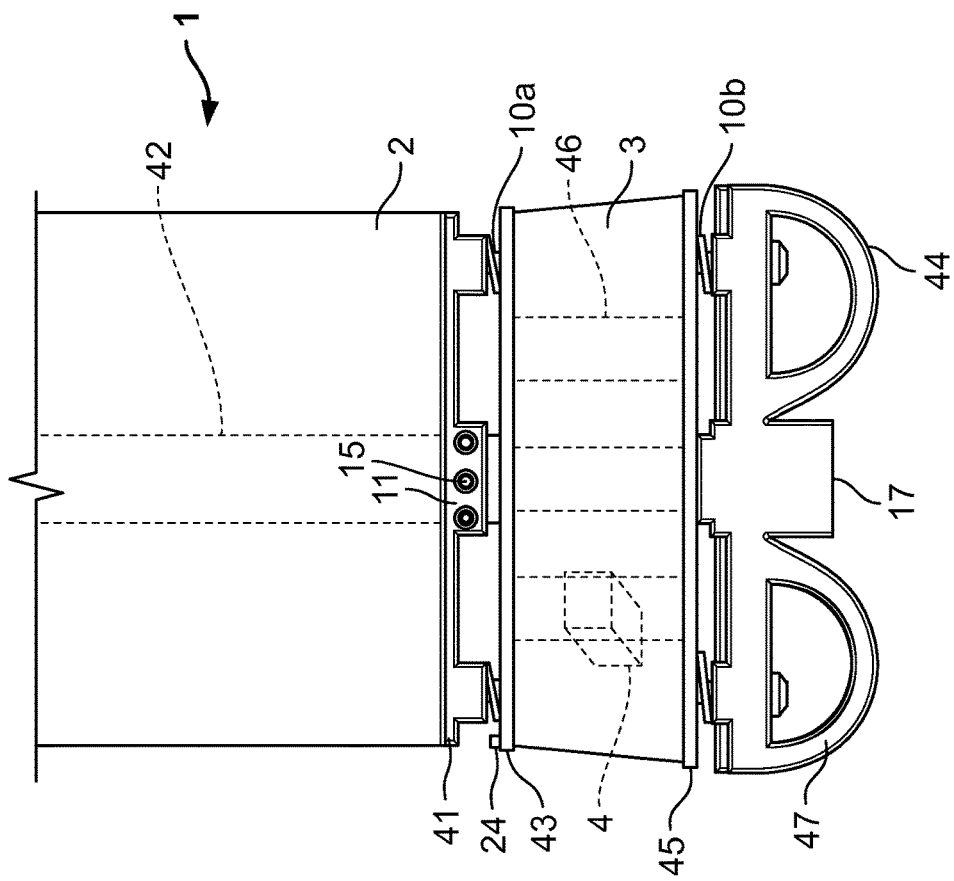
FIG. 4A
FIG. 4B

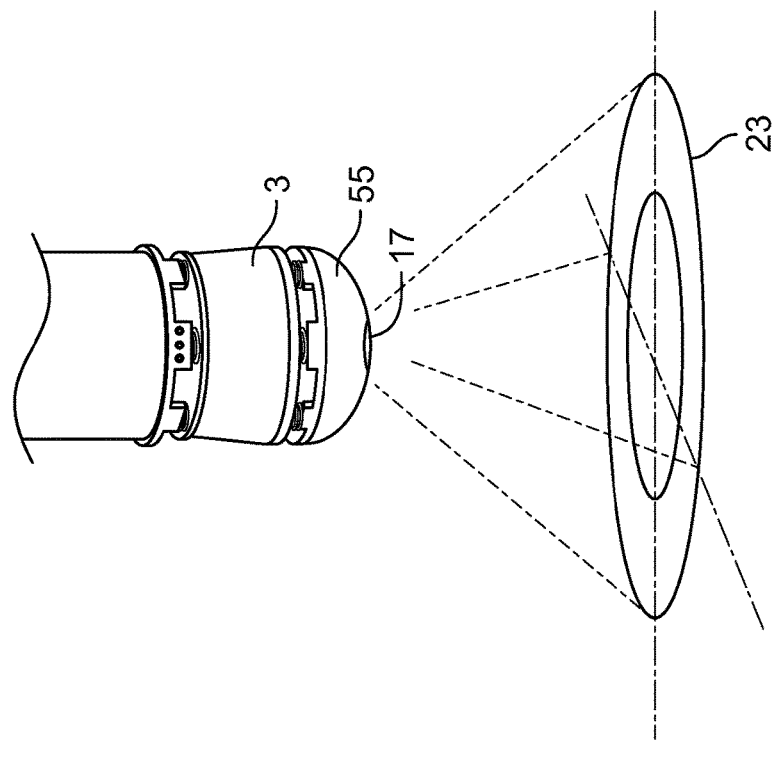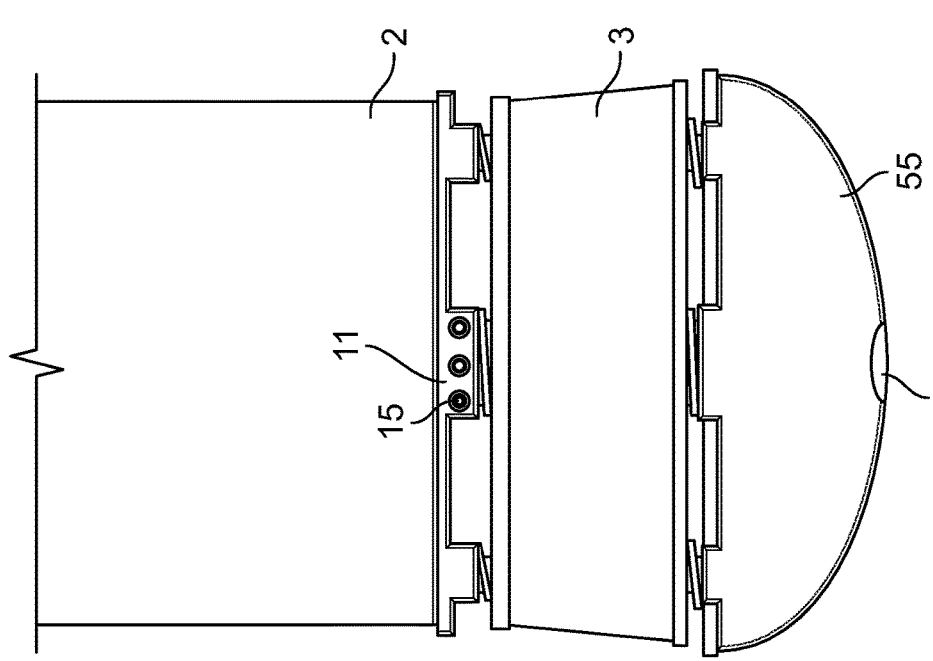

COMPUTERIZED TRAINING PUNCHING BAG

CROSS REFERENCE TO RELATED APPLICATIONS

Applicant claims priority under 35 U.S.C. 119(e) of U.S. Provisional Patent Application Ser. No. 62/200,554 filed Aug. 3, 2015 and of U.S. Provisional Patent Application Ser. No. 62/200,792 filed Aug. 4, 2015 the disclosures of which are incorporated by reference.

BACKGROUND OF THE INVENTION

1. Field of the Invention

This invention relates to an improved punching bag that can be used to train boxers or to perform a new form of exercise workout.

Boxing is a sport that requires lots of practice in order to achieve proper accuracy and force. If there is a device which can measure the performance of a boxer, then boxers will understand their movements and will be helped in improving their boxing skill.

2. The Prior Art

A known punching bag is shown in FIG. 1A and has no electronics to communicate with the boxer or to give feedback about the training or punching performance. An exercise ProStrike® Free Standing Heavy Punch Bag® shown in FIG. 1G and a training shield to be punched shown in FIG. 1F have similar deficiencies. A Sporteq® bob dummy is shown in FIG. 1B and has no electronics. A training device shown in FIG. 1C has no display screen. Devices shown in FIGS. 1D, 1H, 1I, and 1J have simple electronics and are battery-powered and do not have continuous display screens. The Eastpoint Sports Majik® Jab and Bob is shown in FIG. 1H. The Franklin Sports® Go Pro MMA Inflatable Hitting Bag is shown in FIG. 1I. The Amber Sports® Slam Man® shown in FIG. 1J must be filled with sand if the device is to nave stability. The Nexersys® cardio boxing exercise equipment shown in FIG. 1E provides increased communication with the exerciser/trainee but the flat screen projects forwards and the exerciser/trainee stands in the same spot throughout the training.

Accordingly, a need exists for an improved punching device which provides enhanced communication with a trainee, improved tracking of training performance, increased variety in prompting trainee movement, and increased engagement of the intelligence of the trainee as the training is undertaken.

SUMMARY OF THE INVENTION

An electronic punching bag is provided that includes an elongate bag, a microprocessor, and a display screen. The elongate bag is formed of resilient material. The microprocessor is disposed in an interior of the electronic punching bag or at a periphery of the electronic punching bag. The display screen extends around more than half of the periphery of the electronic punching bag and is configured to receive signals from the microprocessor. The signals cause the display screen to display visual signals.

BRIEF DESCRIPTION OF THE DRAWINGS

Other objects and features of the present invention will become apparent from the following detailed description considered in connection with the accompanying drawings. It should be understood, however, that the drawings are designed for the purpose of illustration only and not as a definition of the limits of the invention.

In the drawings, similar reference characters denote similar elements throughout the several views.

FIG. 4A is a perspective view of a lower portion of a further embodiment of the electronic punching bag with a frame cage protective device. FIG. 4B shows the bag of FIG. 4A being suspended from the floor.

FIG. 5A is a perspective view of a lower portion of another embodiment of the electronic punching bag with a soft pad protective device. FIG. 5B shows the bag of FIG. 5A being suspended from the floor.

DETAILED DESCRIPTION OF THE PREFERRED EMBODIMENTS

Figure 1A:
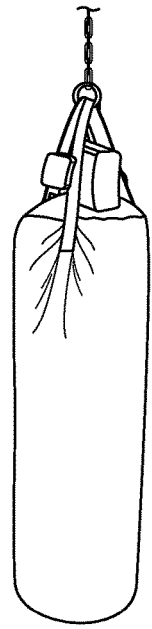
FIGS. 1A-1J show views of the prior art training devices as described above.
Figure 1B:
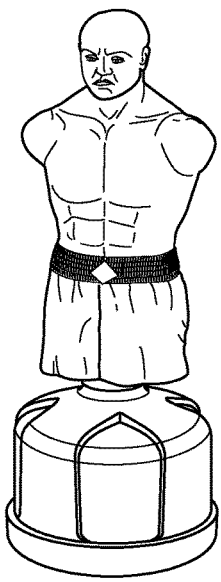
Figure 1C:
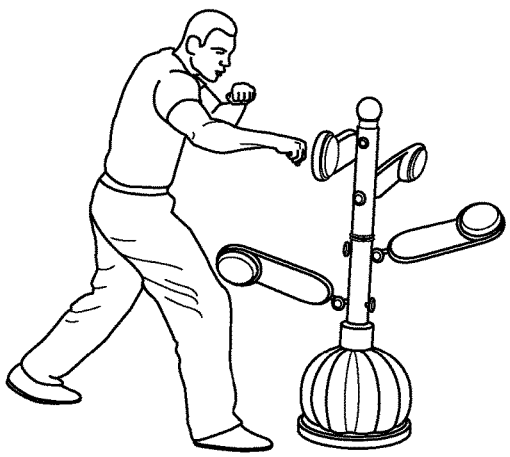
Figure 1D:
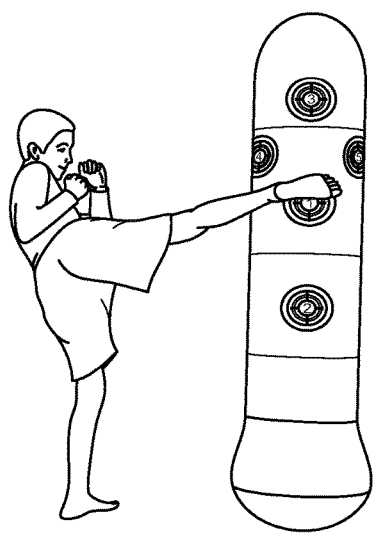
Figure 1E:
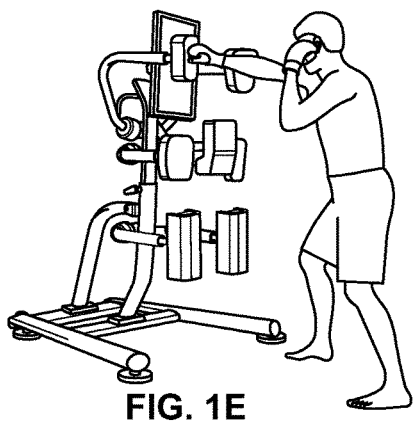
Figure 1F:
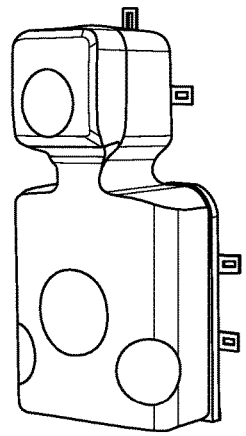
Figure 1G:
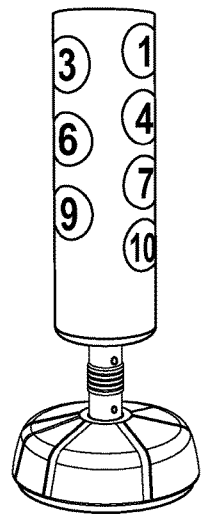
Figure 1H:
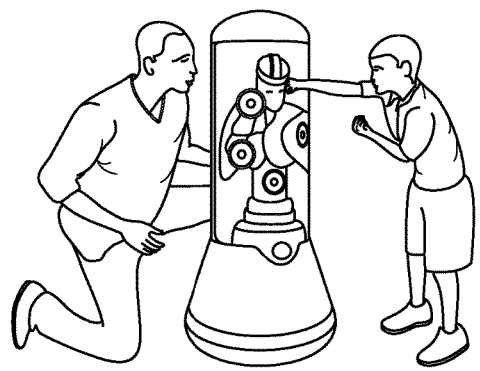
Figure 1I:
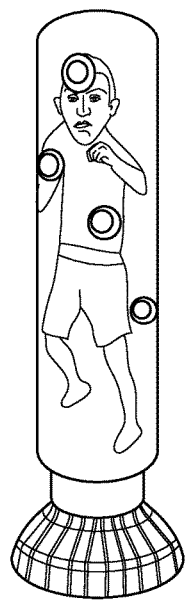
Figure 1J:
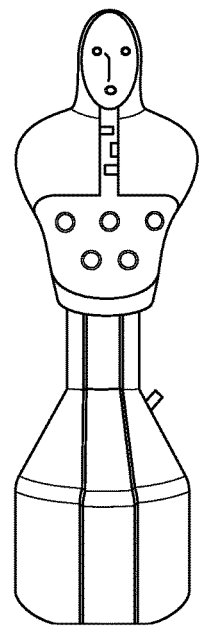

In any sport, especially contact sports, the ability to react on impulse is ideal.

Using a digitally-timed lighting system, the electronic punching bag described herein improves impulsive reactions and a host of other dynamic movements of the boxer/athlete who trains with it. The boxer/athlete is trained to improve his or her visual perception and thought processing in relation to coordinated movements. The pattern and target symbol challenge the spatial intelligence and visual awareness of the boxer. The articulation between visual recognition, comprehension, and mobility skills is challenged.

The device mainly uses non-verbal communication. Physical responses are tracked to provide a solid scale for software to analyze speed improvements and performance. The bag tracks improvement of the boxer. Tracking the reaction time is an optional feature that allows an acceptable delay to be set and can be controlled by the user for a particular level of difficulty. The task will only be considered accomplished and posted on a performance review if it is completed within the set time.

Neuro-transmission occurs instantaneously with thought. Millions of electrical impulses convert dormant motor neurons to action potentials. Action potentials are electrical pulses that travel neuron to neuron to form nerve networks that link brain to muscle neural activity. The pulses conduct and transfer information from brain to muscle at electrifying speeds. All movements in regards to graded force, motion speed, or precision are direct responses to the recruitment and transmission of action potentials.

Can we only move as fast as we think? For instance if someone unexpectedly took a swing at two people, and one person flinched but the other ducked, we see two different reactions to the same stimulus. Nevertheless, both subjects reacted before thinking. Studies have shown that humans have reflex pathways that entirely circumvent our brain. They are amongst the quickest response mechanisms. But can these mechanisms be trained and why did the one person flinch and the other duck? Perhaps the person who ducked had his muscle memory trained from some physical activity in the past or perhaps the person who ducked perceives visual information faster than the other person.

Without seeking to answer these questions conclusively, the electronic punching bag described herein helps train muscle memory by inducing repeated physical activity and by testing the boxer to continue to think and process visual information even when he or she is tired. The precision bag flashes tasks with light, because light has a high speed of travel like electrical energy has.

The electronic punching bag also is useful in the field of rehabilitative work for those individuals who have acquired brain injuries such as through a stroke or trauma or in countering brain degenerative diseases such as Parkinson's Disease. It is now generally accepted that acquired brain injuries, such as occur in stroke or trauma, initiate a cascade of regenerative events that last for up to several weeks if not months. Many investigators have pointed out striking parallels between post-injury plasticity and the molecular and cellular events that take place during normal brain development. Behavioral experience is the most potent modulator of brain plasticity. Based on the quantity and quality of motor experience, the brain can be reshaped after injury in either adaptive ways. Boxing develops physical strength, breath control, and helps teach an individual to stay focused under stress. These benefits of boxing all just happen to be the stimulants needed for neuro-plasticity to kick in.

By using its sequences of numbers, letters, shapes, colors, equations, and/or questions, the electronic punching bag adds brain stimulation to a physical training exercise and becomes a neuro-plasticity rehabilitation tool.

The electronic punching bag also facilitates intense exercise that counteracts the symptoms of Parkinson's Disease. The electronic punching bag helps the boxer improve, train, and strengthen balance, hand-eye coordination, speed of movement, and agility.

By using its sequences of numbers, letters, shapes, colors, equations, and/or questions, the electronic punching bag infuses up to five different intelligence-to-athleticism connections, meaning answers to various equations act as designated points to impact over one or more symbolic matrices of target symbols on the bag, for example over three matrices of target symbols on the bag.

Figure 2:
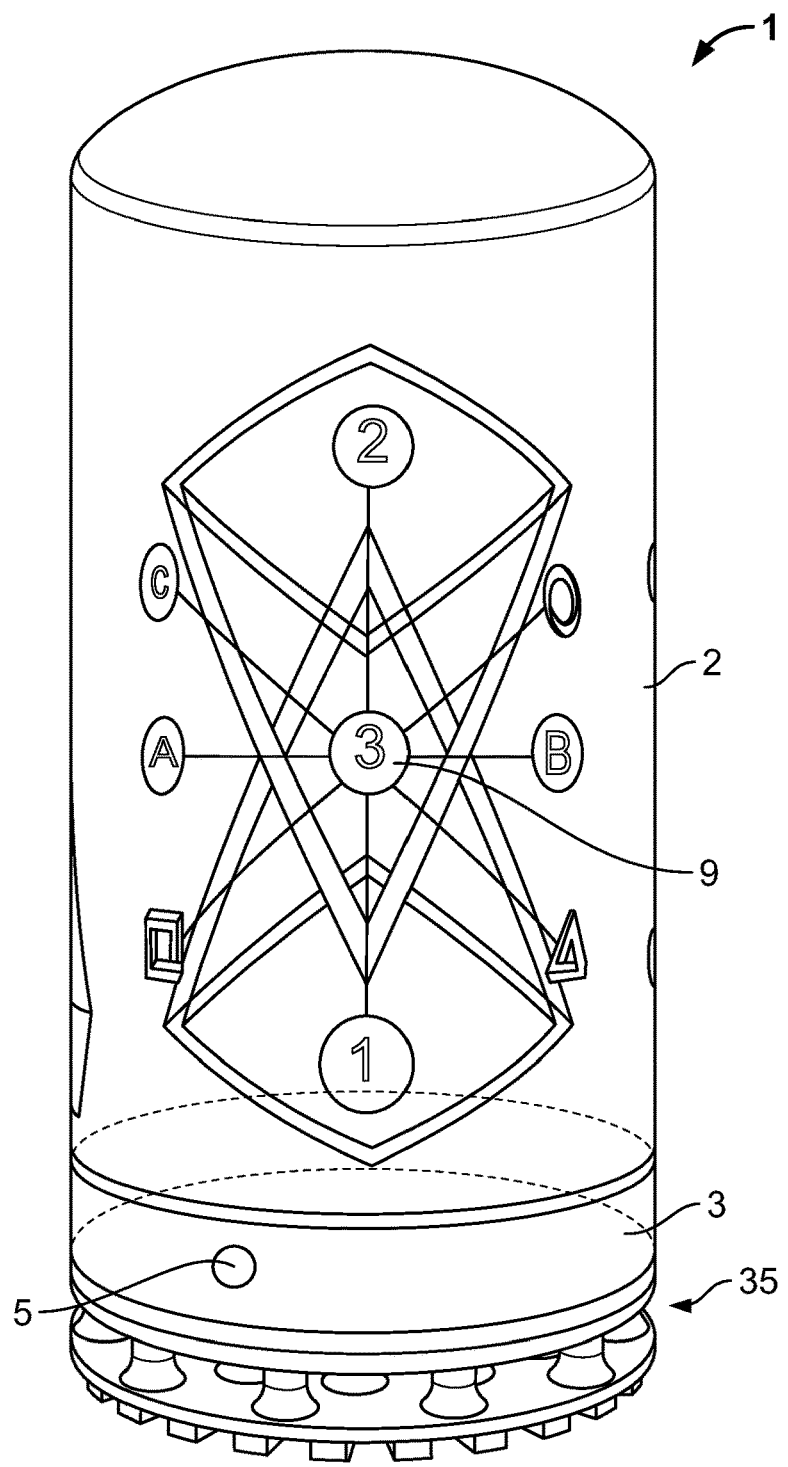
FIG. 2 is a perspective view of one embodiment of the electronic punching bag according to the invention.

Turning now in detail to the drawings, the electronic punching bags 1 shown in FIGS. 2-8A each have a display screen 3 which extends around more than half of the periphery of the electronic punching bag 1. In FIG. 2, the display screen 3 is shown with dotted lines as it extends around to the rear side. The dotted lines show that for this embodiment the display screen 3 extends around the complete periphery of the electronic punching bag 1.

The display screen can extend, for example around 60% or more of the periphery of the electronic punching bag 1, or around 70% or more of the periphery of the electronic punching bag 1, or around 80% or more of the periphery of the electronic punching bag 1, or around 90% or more of the periphery of the electronic punching bag 1, or around 95% or more of the periphery of the electronic punching bag 1, or around the entire periphery of the electronic punching bag 1.

Because the display screen 3 extends around more than half of the periphery of the bag and can extend completely around the periphery of the bag, the display screen 3 can display an image or a visual signal 5 and give the appearance that the image or visual signal 5 moves around the bag clockwise or counter-clockwise. This moving image or moving visual signal 5 leads or prompts the boxer/athlete being trained to follow the image or signal 5 and move himself or herself clockwise or counter-clockwise around the bag 1.

The electronic punching bag 1 will help athletes improve their performance by making it possible to train their physical and mental capabilities. With electronics and software integrated into the bag, the electronic punching bag 1 enables customized exercise which involves visual stimulus processing and reaction tracking. The bag 1 makes it possible to measure the reaction time of the boxer/athlete with respect to the visual stimulations when the boxer/athlete is fatigued. The bag 1 allows for pre-programmed trainings and an ability to integrate new trainings according to the boxer/athlete's needs.

The electronic punching bags 1 shown in FIGS. 2-8A each have an elongate bag 2 formed of resilient material. The elongate bag 2 in one embodiment is cylindrical. The elongate bag 2 can withstand being punched by the boxer who is training using the electronic punching bag 1. Centrally located in the elongate bag 2 may be a piping core that is standard for heavy punching bags. The resilient material may be that used in known punching bags or in known heavy punching bags.

The display screen 3 can be an LED matrix display or an LCD monitor that is a computer screen. In one embodiment the display screen 3 can project a digital image or visual signal 5 in a manner that gives the appearance that the digital image or visual signal 5 moves clockwise or counter-clockwise around the display screen 3. Implied in the definition of display screen is that the screen extends continuously or essentially continuously around the periphery and not in merely unconnected individual sections. For those embodiments in which the display screen 3 is an LED matrix, the LED matrix is flexible. The flexible LED matrix would include LED flashes, LED matrix drivers drive the LED matrix or matrices.

The display screen may be assembled by being manufactured in multiple separate curved sections. The curved sections would be affixed to the bag or frame and aligned next to each other such that the display screen appears to extend continuously around the periphery. Despite these various sections, the assembled display screen functions as a continuously extending screen around the bag. For example, the display screen could be formed from four curved sections, each of which extends over an arc of 90 degrees, so that when all four curved sections are fixed to the bag and aligned with each other, the display screen extends around all 360 degrees of the bag in a ring shape. The display screen could be formed from two such sections extending around 180 degrees. The display screen could be formed from three such sections each extending 120 degrees. For those embodiments in which the display screen extends around more than half of the periphery of the bag but not around the complete periphery of the bag, the display screen could still be manufactured in multiple separate curved sections. For example, for a display screen that extends around two/thirds of the periphery of the bag, the display screen could be formed from two separate curved sections which each extends around one/third of the periphery of the bag.

The visual signals 5, e.g. an array of colored lights or graphic effects, can be displayed on the display screen 3 at various positions around the periphery of the bag 1 so that via the signals 5 the boxer can be prompted to move to various positions clockwise or counter-clock-wise around the bag 1 to punch at various positions on the bag 1 dispersed clockwise or counter-clock-wise around the bag 1. The visual signal 5 can randomly pause or switch speeds and directions at any time. The boxer is in one training session embodiment expected to stay within arm's reach of the visual signal 5 at all times. Once the visual signal 5 stops, the display screen 3 can display or flash patterns 7 that may be a number or a color to indicate to the boxer what punch or punch combination should be thrown and to what part of the elongate bag 2. Under a more advanced training program, a pattern 7 could flash indicating a punch should be thrown even while the visual signal 5 moves. This moving pattern 7 causes the boxer to need to punch while he or she moves.

Figure 7A:
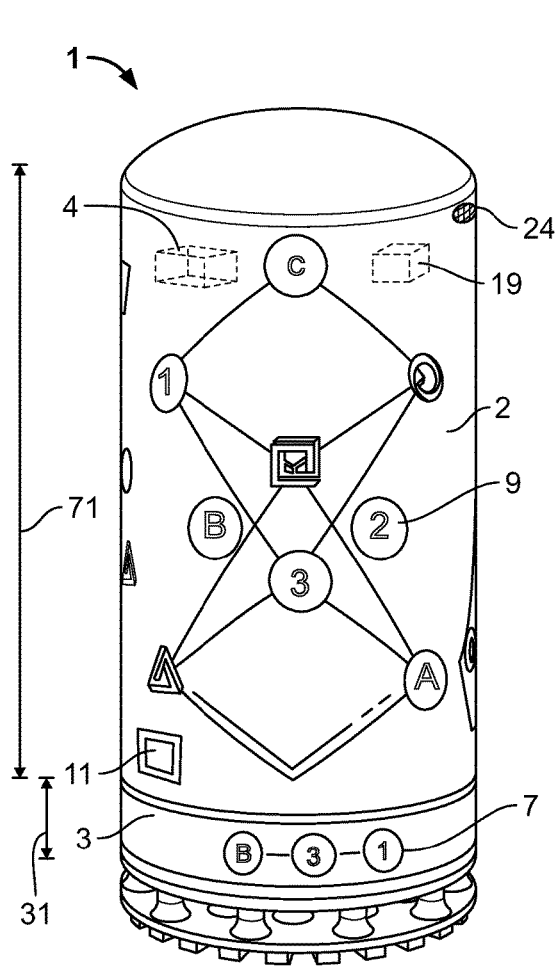
FIGS. 7A-7D show perspective views of different embodiments of the target symbols disposed on the electronic punching bag.
Figure 7B:
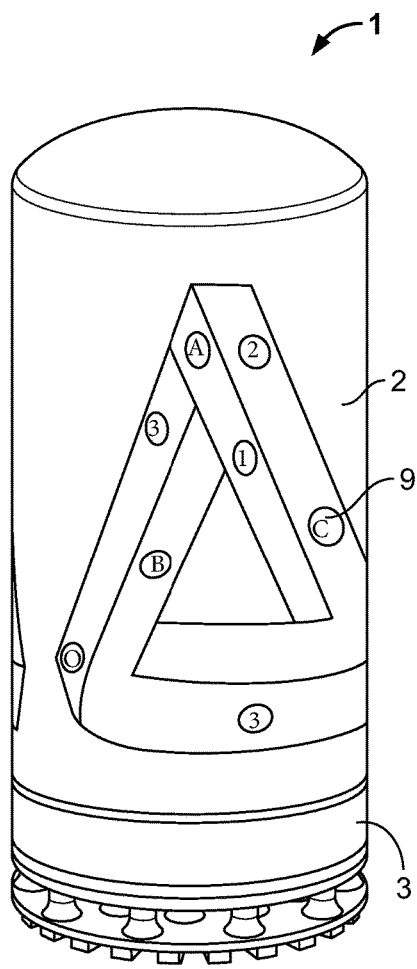

In the embodiments of the electronic punching bag 1 shown in FIG. 4A and in FIG. 7A, the microprocessor 4 is shown. In these embodiments, the microprocessor 4 is disposed in an interior of the electronic punching bag. The microprocessor 4 may also be disposed at a periphery of the electronic punching bag 1. The embodiment shown in FIG. 7A includes the microprocessor 4 being disposed in an upper region of the elongate bag 2, but the microprocessor 4 will usually be disposed in a display screen portion 35 of the bag 1 interior from the display screen 3 and protected by the shock absorbing section. FIG. 4A shows this usual positioning of the microprocessor 4, with the microprocessor 4 being shown in dotted lines due to it not being visible from the exterior of the bag 1 and being positioned behind the display screen 3.

The microprocessor 4 is configured to send signals to the display screen 3 to control the display screen 3 and to cause the display screen 3 to display the visual signals 5 and patterns 7 such as colors, identifications, symbols, or a question such as an equation. The microprocessor 4 includes memory storage and may also be connected with a separate memory storage device for enhanced memory space. Predefined training programs can be saved in the memory storage or in the separate memory storage device. Training programs could be wirelessly transmitted to the microprocessor from a smart phone and the memory could save the newly-uploaded/downloaded training program. The microprocessor is programmed with software to cause the bag 1 to execute the training program. The microprocessor 4 can be disposed on a printed circuit board.

Figures 3A, 3B:
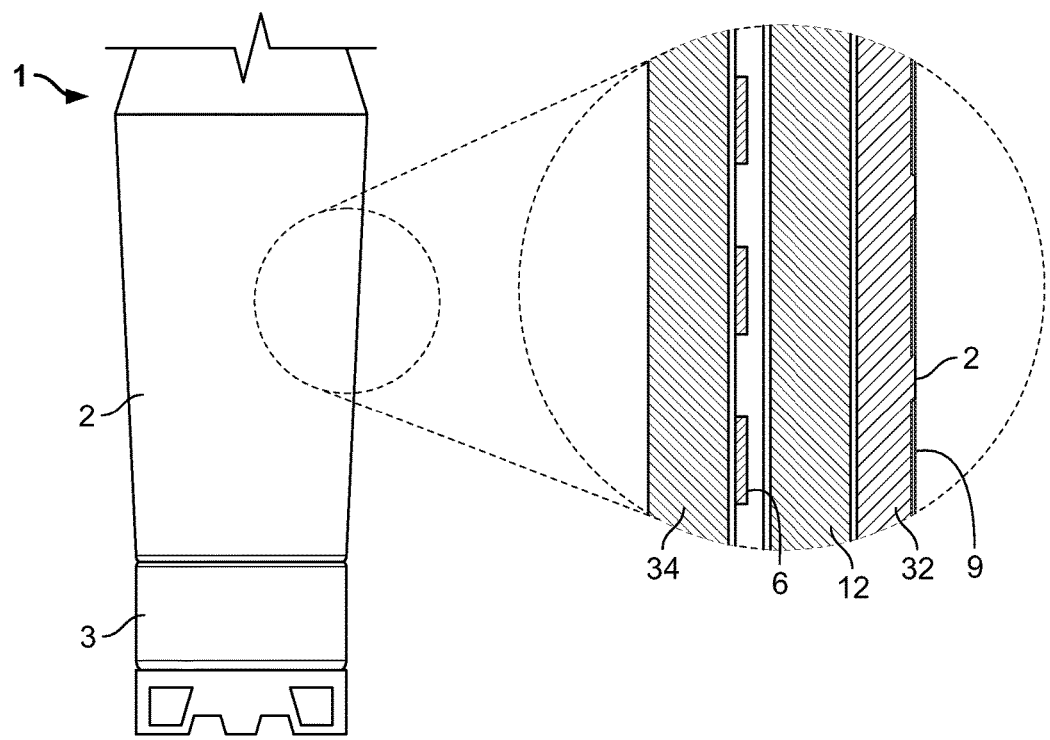
FIG. 3A shows a perspective view of an embodiment of an electronic punching bag according to the invention.
FIG. 3B shows a cross-section through the electronic punching bag of FIG. 3A in which sensors are visible embedded in the bag.
Figure 3C:
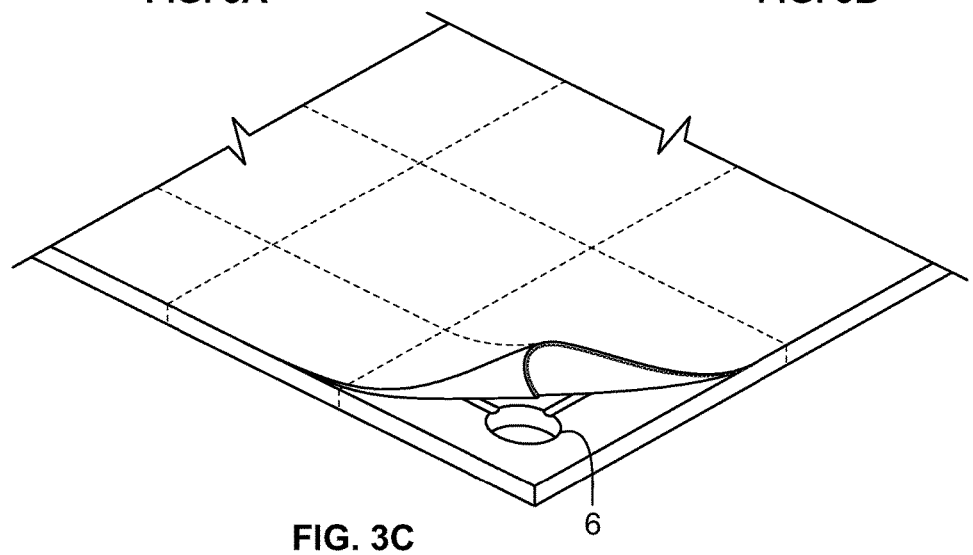
FIG. 3C shows a view of resilient material in which sensors are embedded before it is manufactured into part of a punching bag.

FIGS. 3B and 3C show sensors 6 that are embedded in the elongate bag 2 in order to sense punching performance of a boxer using the electronic punching bag 1. A plurality of sensors 6 are distributed throughout the elongate bag 2. In one embodiment, the sensors 6 can be embedded from one to two inches into the interior from the exterior surface of the elongate bag 2. FIG. 3B shows a cross-section of an exterior portion of the elongate bag 2 of the electronic punching bag 1 from FIG. 3A. FIG. 3B shows that in this embodiment the sensors 6 are disposed between an absorbing foam layer 12 and a supporting foam layer 34. An outer covering layer 32 contacts the absorbing foam layer 12. The outer covering layer 32 can be made of vinyl or canvas or leather or a similar material. The sensors 6 are impact sensors so that each sensor can sense an overall force absorbed by the sensor 6. The sensor 6 could also give a binary indication of positive or negative as to whether a punch has been landed with some error of margin. The sensors can also recognize the accuracy of a punch to sense whether the punch was a direct hit or only a partially direct hit.

The sensor technology can be similar to the sensor technology implemented in a Daedo® electronic body protector worn by kickboxers.

FIGS. 2 and 7A-7D show target symbols 9 disposed on an exterior of the elongate bag 2. Each target symbol 9 is aligned with a respective sensor 6, as is shown in FIG. 3B. The target symbols 9 may be a character, another symbol, a shape such as a square, a triangle, or a circle, and also may have a particular color incorporated therein. The target symbols 9 may be divided into groups or symbolic matrices distributed around the periphery of the bag. For example, the electronic punching bag may include three symbolic matrices of nine target symbols each so that the embodiment has a total of twenty-seven target symbols distributed around the bag. Each matrix of target symbols may constitute a symbolic puzzle or a brain maze. In another embodiment, the electronic punching bag may include three matrices of six target symbols each so that the embodiment has a total of eighteen target symbols distributed around the bag. The target symbols 9 cans glow in the dark.

For the embodiment with a total of twenty-seven target symbols 9, the electronic punching bag 1 would usually have at total of twenty-seven sensors 6 embedded in the electronic punching bag, with each sensor 6 being aligned with a particular target symbol 9 so that the sensor 6 senses a punch to the bag 1 at that target symbol 3. Optimized placement of the sensors 6 in the bag 1 improves the durability and sensitivity of the electronic punching bag 1.

The sensors 6 are connected with the microprocessor 4 to send sensor signals to the microprocessor 4. Due to this connection, the sensing of the sensors 6, and the processing ability and memory of the microprocessor 4, a punching performance of a user using the electronic punching bag can be tracked via the microprocessor 4. The connection between the sensors 6 and the microprocessor 4 can occur via wiring or via a wireless connection. FIG. 3C shows a sensor 6 which senses pressure and which has a physical wiring connection that runs from it to the microprocessor and possibly to other sensors 6.

The signals from the microprocessor 4 to the display screen 3 cause the display screen 3 to display at least one visual signal pattern 7 representing at least one target symbol 9 of the elongate bag 2. Thus, when the boxer sees the pattern 7 he or she then knows which target symbol 9 on the elongate bag to punch. For example, the pattern 7 may be a yellow "3" or a red "A" prompting the boxer to punch the yellow 3 or the red A that is visible on the bag. The patterns 7 can be in the form of variously colored lights, colored cursors, symbols, shapes, and/or a fireball which match with certain color regions on the punching region of the bag so that the display of a particular pattern 7 on the monitor, i.e. the display of a red light, would prompt the boxer to punch a red colored region in the elongate bag 2 above the display screen 3.

The patterns 7 cam be given in combinations to prompt the boxer to throw a particular combination of punches at certain regions and target symbols 9 of the punching bag. The pattern cursor could move and then stop and flash a color code to prompt the boxer to throw a particular punch combination. In one instance, the pattern 7 is displayed on the display screen 3 as a quick succession of a green pattern, then a yellow pattern, and then a red pattern indicating to the boxer that he or she should punch the green target symbol 9, then the yellow target symbol 9, and then the red target symbol 9. In one embodiment, the target symbols 9 do not light up and each target symbol maintains a permanent color. In another embodiment, the target symbols 9 themselves could light up. For example, FIG. 7A shows the punch combination B-3-1 which prompts the boxer to sequentially punch target symbols labeled as B, 3, and 1 on the elongate bag 2.

The pattern 7 could also signal to the boxer to perform other intermittent exercises, such as for example to perform five jumping jacks.

Figure 7C:
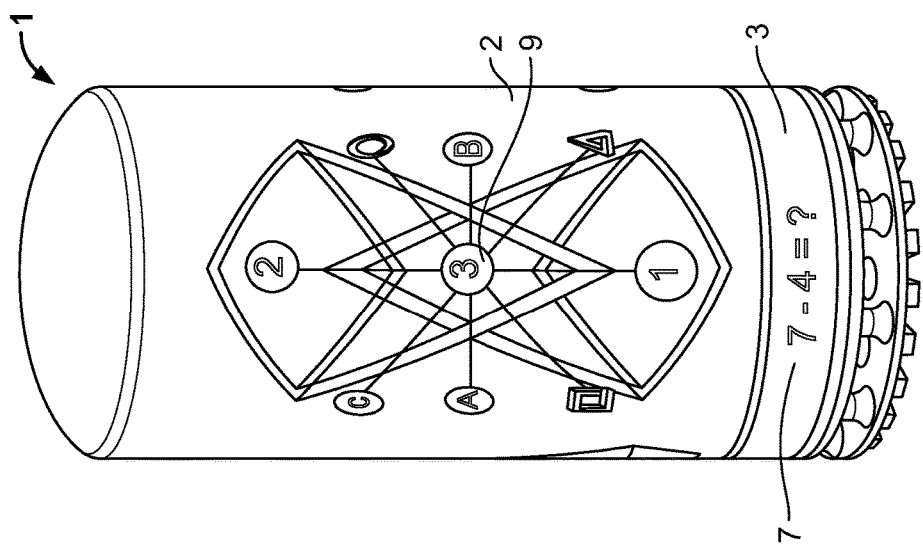

The pattern 7 can also be an equation or a question, and a correct answer to the question corresponds to at least one target symbol 9. For example, as shown in FIG. 7C the pattern 7 can be the equation 7 minus 4=? When the boxer, sees the equation he can calculate in his or her mind that the answer to 7 minus 4 is three. This equation is, therefore, a prompt to the boxer/athlete that he or she should punch the target symbol designated with a "3" on the elongate bag 2.

The display screen 3 could show two symbols moving towards each other, one being a bland target symbol and one matching a target symbol 9 on the bag. When the two symbols reach each other on the screen and overlap, this is the signal for the boxer to punch the target symbol 9 on the elongate bag 1 which matches the display screen symbol.

The equation or question could also include IQ test questions in which multiple groups of symbols are shown, and the boxer must identify what is the same or different from the various groups of symbols. The answer to this riddle matches at least one target symbol 9 on the elongate bag and thus, the boxer is prompted to punch that particular target symbol.

Thus, with this feature the electronic punching bag 1 can help an athlete achieve enhanced training because his or her thinking and reasoning abilities are tested even when he or she might be weary from the workout. The pattern 7 can also give information about what type of punch should be thrown, such as a right or left body shot, a right or left upper cut, a right straight jab or a left straight jab, a right or left hook, or a combination of these punch types. A video camera disposed in the device could record the boxer to determine and sense and communicate to the microprocessor 4 whether the proper punch type was punched by the boxer.

The electronic punching bag 1 and its screen 3 and its light 17 help encourage the boxer/athlete to move, help challenge his or her lateral agility, help develop his or her hand-eye coordination, help build endurance, and help the boxer to learn to stay focused.

The microprocessor 4 can have a built-in timer so that the microprocessor 4 can track the reaction time of how long it takes the boxer to land a punch at the correct target symbol based on a particular pattern 7 being displayed at the display screen 3. The timer can track with an accuracy in milliseconds. Thus, with this embodiment of the microprocessor 4 it is possible to track the performance of the boxer during fatigue conditions. The boxer is generally given a time of from one to three seconds from the displaying of the pattern 7 until he or she is expected to land the punch at the target symbol 9 that corresponds to the particular pattern 7 that was displayed. Via the control unit 11 or via a smart phone communicating wirelessly with the bag 1, the boxer could control the difficulty level of the training session to adjust how much time can elapse between the pattern 7 display and landing a punch in order for the punch to be considered timely.

The electronic punching bag 1 will be formed with synchronization between the display screen 3, the patterns 7 generated at the display screen 3, the sensors 6, and the built-in timer of the microprocessor 4 so that the performance of the boxer is accurately evaluated.

The microprocessor 4 is also configured to receive and transmit a wireless signal and to receive instructions via the wireless signal.

The microprocessor 4 can generate a performance report about the success of the boxer with respect to (1) his or her timely punching of the correct target symbols and/or (2) the power of the punches thrown and/or (3) the accuracy of the punches thrown and/or (4) the types of punches thrown. In the report, one number could be a total punch count and another number could be an impact punch count. The report can include a review graph. Only punches delivered within a specified reaction time would qualify as an impact punch. The reaction time could be, for example, less than one second or less than three seconds. The microprocessor 4 can wirelessly send this performance report to another computer or to a handheld computer device. For example, the electronic punching bag 1 may be equipped with a transmitter 19 to allow a wireless communication between the microprocessor 4 and a handheld smart phone so that the microprocessor 4 sends the performance report to the smart phone. The transmitter could in one embodiment receive and transmit short-wavelength ultra-high frequency radio waves, e.g. could be a Bluetooth® transmitter 19.

Via the transmitter 19, the bag 1 could also communicate with a heart-rate monitor that is worn by the boxer/athlete.

The microprocessor 4 could alternatively send this performance report to be displayed at the screen of the control unit 11 or on the display screen 3. The microprocessor 4 could also communicate information about the report via the audio speaker 24 to give encouragement or correction to the boxer during the training/punching session.

Likewise, an exerciser can determine a particular program or routine to use for a training session and can make a selection on his or her smart phone of the program or routine to be implemented by the electronic punching bag. Via the Bluetooth® wireless communication 19, e.g. shown in FIG. 7A, the selection can be sent to the microprocessor 4 so that the microprocessor 4 will control the electronic punching bag 1 and the display screen 3 to implement the selected training program. In other words, in this embodiment the wireless communication feature supplements or obviates the need for the control unit 11.

The microprocessor 4 may also be programmed with multiple training programs so that upon its arrival and initial setup in a home or a gym, these training programs can be undertaken by a boxer.

The electronic punching bag may also include a control unit 11 disposed on an exterior of the electronic punching bag 1 and connected to the microprocessor 4. The control unit 11 may include input devices 15 configured to receive programming from a user. In the electronic punching bag embodiment shown in FIGS. 4A-4B and 5A-5B, the input devices 15 are buttons or switches. In the electronic punching bag embodiment shown in FIGS. 6A and 6B, the control unit 11 is an LCD touch screen which acts as a graphical user interface. Via the control unit the user can select a training program or change training regimen variables such as level of difficulty. The control unit can give system and command control. For the embodiment shown in FIGS. 6A and 6B with the LCD touch screen control unit 11, the control unit 11 may have a processor that is in addition to the microprocessor 4 in order to handle the heightened processing demands that result from the LCD touch screen control unit 11. The screen control unit 11 can display feedback about the status of the punching bag 1.

In some embodiments, the electronic punching bag also has an audio speaker 24. The audio speaker has a connection to the microprocessor 4 and is capable of giving audio commands and prompts and feedback to the boxer. FIG. 7A shows an embodiment with the audio speaker 24 disposed in an upper region of the bag 1. The audio speaker may alternatively be disposed in the region near the control unit 11 or in some other portion of the bag 1, for example as is shown in FIG. 4A where the audio speaker 24 is disposed slightly above the display screen 3 and below the elongate bag 2.

Figure 6B:
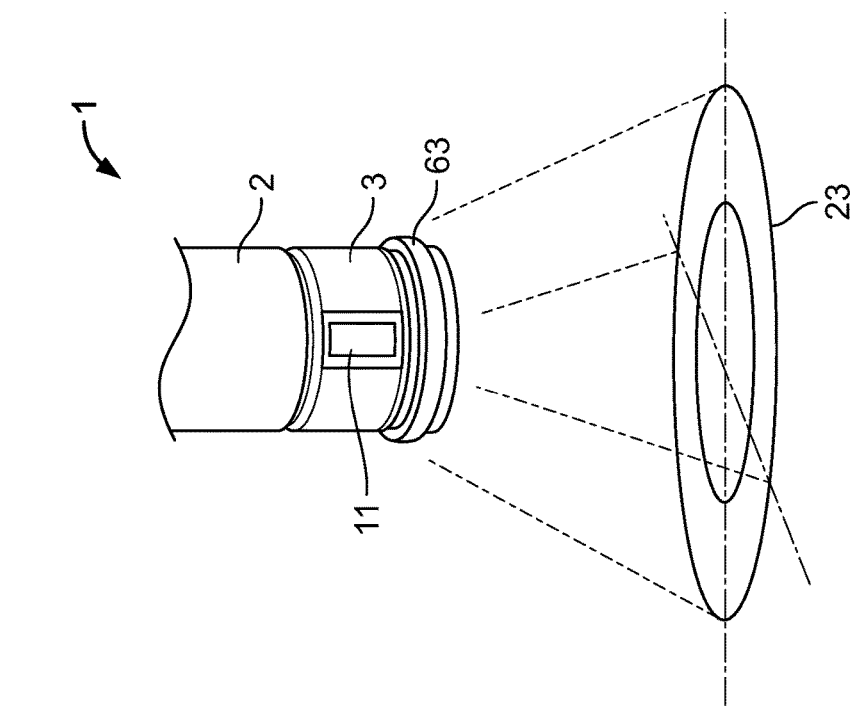
FIG. 6B shows the bag of FIG. 6A being suspended from the floor.

In some embodiments of the electronic punching bag 1, the bag includes a light 17 configured to emit light downwards and to project a line signal 23 on a surface below the electronic-punching bag 1 when the electronic punching bag 1 is suspended in the air above the surface. The surface would usually be the floor on which the boxer is standing. This line signal 23 gives visual instructions to the boxer as to how he or she should position his or her depth with respect to the punching bag 1. For example, the line signal 23 can move to prompt the boxer to move closer in next to the bag 1. Alternatively, the line signal 23 can move to prompt the boxer to move further away from the bag. The light 17 may be a laser light. FIGS. 4B, 5B, and 6B show an example of an electronic punching bag embodiment with the light 17 that can be a laser light.

As shown in FIG. 4B, 5B, or 6B, the line signal 23 can be two concentric circles centered around a longitudinal axis of the bag 1. In one embodiment, the circles growing in size can prompt the boxer to distance himself or herself from the bag 1 and the circles decreasing in size can prompt the boxer to move closer to the bag 1.

Figure 6A:
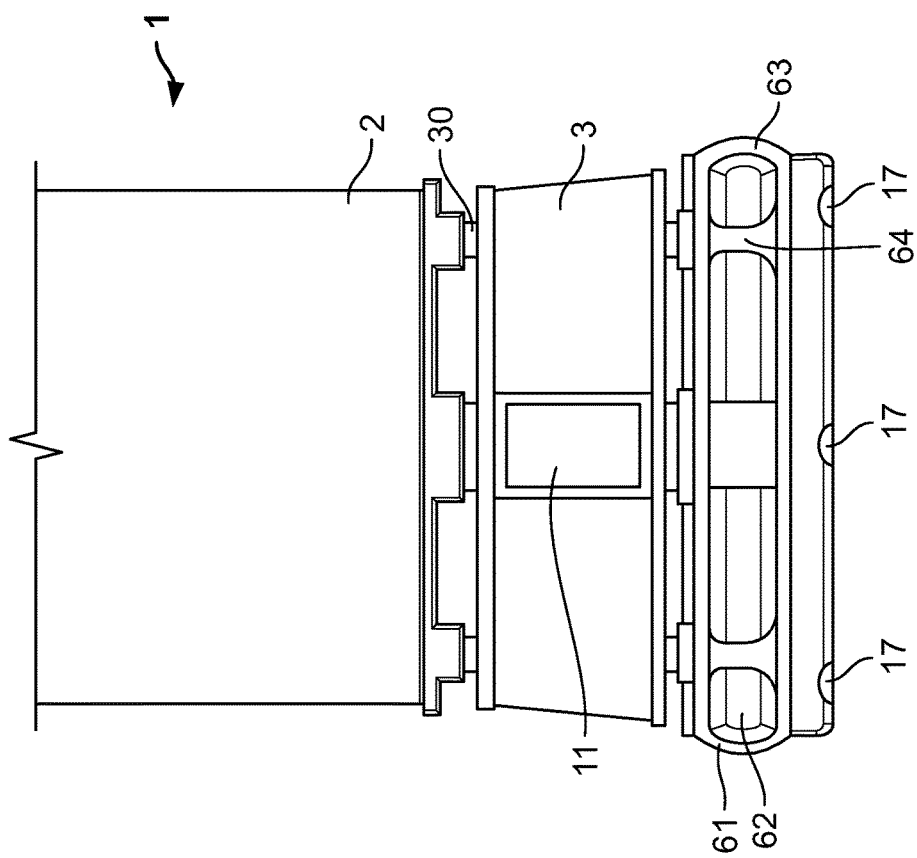
FIG. 6A is a perspective view of a lower portion of another embodiment of the electronic punching bag with an air bag protective device.

FIGS. 4A and 5A show an embodiment with a light 17 disposed at a central portion of the bottom of the bag 1. FIG. 6A shows an embodiment with a series of lights 17 distributed around a periphery of the bottom of the bag 1.

The signals from the microprocessor 4 to the display screen 3 cause the display screen 3 to display a sequence of movement of visual signals 5 and display of patterns 7 which together constitute a boxing training regimen.

In one embodiment, the training regimen can include a fight choreography of a past boxing match. For example, the movement and punch combinations of Joe Frazier from his 1971 fight versus Muhammad Ali can be tracked and recorded and programmed as a sequence of movements of the signal 4 and display of patterns 7 such that the sequence represents a choreography of Joe Frazier during his fight. A boxer who moves and punches according to the sequence of the prompts from the screen 3 of the bag 1 mimics the movement Joe Frazier did during his fight and mimics the punches thrown by Joe Frazier during his fight. In another fight choreograph program, the microprocessor 4 is programmed with a choreograph of Floyd Mayweather, Jr. according to his movement and punching in his 1998 fight against Genaro Hernández that lasted eight rounds.

The fight choreograph program would pause and give the boxer a break between each round. The pause could last, as long as the actual fight pause of the historic boxing match or could be a reduced time length. The user could adjust the pause time between rounds using the control, unit 11.

The fight choreography program or training regimen program is saved in the microprocessor 4. A boxer using the bag 1 can select the program using the control unit 11 or using his or her computing device if the bag 1 has a wireless transmitter/receiver. The bag 1 could be pre-programmed with several such choreographs. A gym or an individual user could also purchase additional fight choreographies from a central computer database to upload these additional fight choreographies to his or her electronic punching bag 1.

The professional fight choreography can be loaded as a program and packaged with short video clips and a punch glossary. Professional boxers could also market training programs to be programmed into the electronic punching bag. The consumer could download a training program from the professional boxer that would prepare him or her for the choreographed fight, and then after completion of the training program the boxer could undergo the choreographed fight with the electronic punching bag prompting him or her for each part of the choreography.

The display screen is disposed in a display screen portion 35 of the electronic punching bag. FIG. 2 shows the display screen portion 35 being disposed at a bottom of the punching bag 1, i.e. below the elongate bag 2 formed of resilient material. The embodiments of FIGS. 4A to 7D also have the display screen portion at a bottom of the punching bag 1. FIGS. 8A and 8B show alternative embodiments in which the display screen portion 35 that includes the display screen 3 is disposed at a top region of the bag 1, i.e. above the elongate bag 2 with resilient material.

For some embodiments, at the bottom of the display screen portion 35 is a shock absorbing section that protects the display screen 3 and other electronic components if the bag 1 fails to the ground. The shock absorbing section typically includes at least one shock absorbing device such as a spring 10a or 10b or hydraulics which provides flexibility and cushioning in case the bag 1 were to fall to the ground.

FIG. 4 shows an embodiment in which the shock absorbing section is a protective cage 44 that encases the display screen 3. The protective cage 44 is a solid frame cover, e.g. a metal, plastic, or fiberglass frame cover, around the electric components to protect all of the electric components in case the bag 1 were to fall to the ground. The metal frame embodiment may be formed from aluminum. In a further embodiment, protective foam, e.g. sponge foam, could surround the protective cage.

The protective cage 44 may be formed via three main different structural parts—(1) a bag holding plate portion, (2) a middle plate region, and (3) a strut region.

The bag support plate portion includes a bag support plate 41 underneath the elongate bag 2 and on which the elongate bag 2 rests. The bag support plate portion has a central piping 42 running upwards from the center of the bag support plate 41 to provide a longitudinal inner support for the elongate bag 2.

The middle plate region includes an upper middle plate 43 that is connected to the baa support plate 41 via shock absorbing devices such as springs 10a or hydraulics. The middle plate region also includes a lower middle plate 45 that is connected to the upper middle plate 43 via weight bearing posts 46. The cage 44 may include four, six, or eight or some other number of these weight bearing posts 46.

The weight bearing posts 46 are disposed inside of the outer periphery of the electronic punching bag 1, because the display screen 3 sits in the space between the upper middle plate 43 and the lower middle plate 45 at the outer periphery of the bag 1. The upper middle plate 43 and the lower middle plate 45 can each include a lip to which the display screen 3 can be connected.

The microprocessor 4 will also usually be disposed in the middle plate region between the upper middle plate 43 and the lower middle plate 45 within the interior of the middle plate region. This placement of the microprocessor 4 allows the microprocessor to be close to the display screen 3, the control unit 11, and an audio speaker 24 in order to easily transmit information and signals with these devices. Thus, when the bag 1 is fully assembled with the display screen 3 attached to the upper middle plate 43 and the lower middle plate 45, the microprocessor 4 is disposed inwards from the display screen 3 and is not visible from the exterior of the electronic punching bag 1.

The strut region is disposed at the bottom of the electronic punching bag 1 and is connected to the lower middle plate 45 of the middle plate region via springs 10b or other shock absorbing devices. The strut region includes a plurality of struts 47, with each of the struts 47 extending from near a central region of the electronic punching bag 1 to the outer periphery of the electronic punching bag 1. The strut region could have four struts, six struts, eight struts, or some other number of struts.

The light 17 can be disposed at the center of the strut region but is usually disposed higher upwards than the bottom of the struts 47. Due to this positioning of the light 17, if the bag 1 falls down the bag 1 will land on the struts 47 and will not directly land on the light 17.

FIGS. 5A and 5B show an embodiment of the bag in which the strut region is replaced by a soft pact 55. The soft pad 55 is a soft shock resistant material applied at the bottom of the bag. The soft pad 55 may be formed of an EVA foam. This embodiment is a lighter embodiment due to the lightweight nature of the EVA foam. The soft pad 55 may be rounded to have a hemispherical shape. The soft pad 55 can be connected to the lower middle plate of the middle plate region. In this embodiment, the light 17 can be disposed at a central bottom portion of the soft pad 55 so that the surface of the light 17 is disposed co-planar with the bottom flat or curved surface of the soft pad 55. In another embodiment, the soft paid 55 could be formed from transparent material so that the light 17 is disposed further upwards in the display screen portion and transmits light downwards that runs through the soft pad 55 and still emerges to form line signals 23 on the floor. Alternatively, for this embodiment in which the light 17 is disposed upwards from the soft pad bottom surface, the soft pad 55 could have holes running therethrough which act as a light transmitting chamber for the light 17 to send light downwards to form line signals 23 on the floor.

FIG. 6 shows an embodiment of the bag in which the strut region is replaced by an air bag 63. The air bag 63 helps absorb the shock if the bag 1 falls to the ground. The air bag technology can be similar to air pockets at the bottom of some athletic shoes. The air bag 63 can include a soft plastic frame 61 around one or more air pockets 62 with soft plastic weight bearing posts 64 extending through the air pockets 62. The air bag 63 can be connected to the lower middle plate of the middle plate region. The one or more air pockets 62 are enclosed by an outer transparent window to protect dust or dirt from entering into the air pocket 62. The plastic of the air bag 63 can be polyurethane or a similar plastic material to surround the pockets that are filled with air or some inert gas.

For this air bag embodiment, the springs 10a or other shock absorbing devices between the bag holding plate portion and the middle plate region or between the middle plate region and the air bag region are covered by respective sleeves 30 which prevent dust or dirt from getting lodged in the spring area. The sleeves nevertheless can slide upwards or downwards into openings in the plates when the springs 10a, 10b are compressed or extended due to a compression force.

FIGS. 2 and 7A-7E show an alternative embodiment in which the shock absorbing section has an open configuration. This configuration has air pockets running through it that are open to the exterior. Numerous posts run through the air pockets from a lower flat plate to an upper flat plate. The bottom of this configuration includes numerous ribs running radially on the bag bottom face on the bottom surface of the lower flat plate and distributed spaced from each other around the bottom face periphery. Soft or hard plastic or metal or other materials can be used for the posts, plates, and ribs of this configuration.

FIG. 8A shows an alternative embodiment, of an electronic punching bag 1' in which the display screen portion 35 and the display screen 3 are disposed at the top of the bag 1' instead of at the bottom of the bag 1'. A transform region 84 occurs towards an upper part of the elongate bag 2. At the transform region 84, the resilient material surface of the elongate bag 2 widens, e.g. in a conical manner, up to a maximum-sized cylindrical region at the top of the bag 1'. This transform region 84 can allow a boxer to practice different punches such as an upper cut and a body shot.

FIG. 8B shows an alternative embodiment with a large diameter heavy electronic punching bag 1". This embodiment also includes the display screen portion 35 at the top of the bag 1". The elongate bag 2 is below the display screen portion 35 and a cushioning section 82 is disposed at the bottom of the bag. With this embodiment, the elongate bag 2 can rotate while the display screen portion 35 and the cushioning section 82 remain stationary. Alternatively, the cushioning section 82 and the elongate bag 2 could rotate together while the display screen portion 35 remains stationary.

FIGS. 8A and 8B show a connection accommodation 26 configured to allow the electronic punching bag 1 to connect with a connecting device 22 shown in FIG. 7E so that the bag 1 is suspended above the ground. The connection accommodation 26 could be one or more chain eyelets so that if the connecting device 22 is a chain, the chain can engage with the chain eyelet. The connecting device 22 could also be configured to connect to a rope, a fabric strap, or a fabric rope for low vibration. With the connection accommodation 26 and the connecting device 22, the electronic punching bag 1 can be adjusted to better match a boxer of a different height. Specifically, the connection accommodation 26 could be attached to a different higher or lower portion of the connecting device 22 to achieve this height adjustment.

Figure 7D:
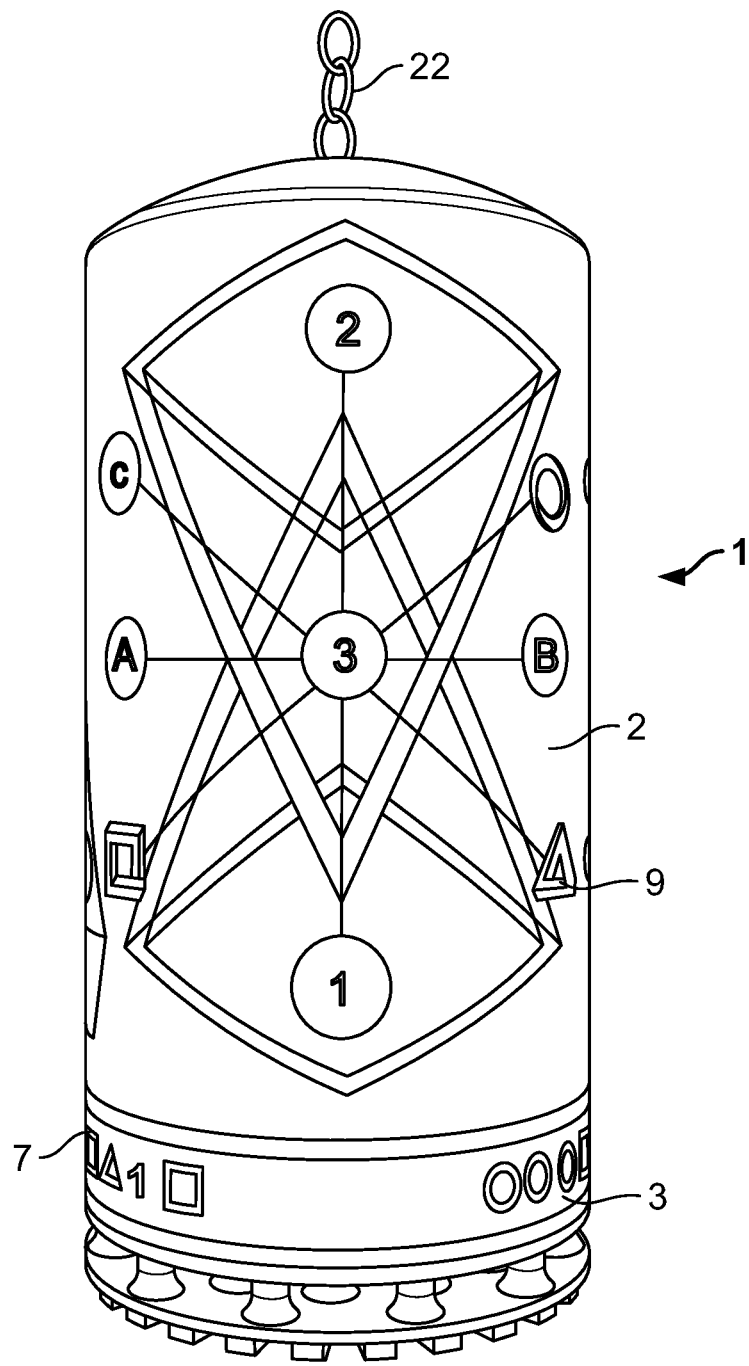
Figure 8A:
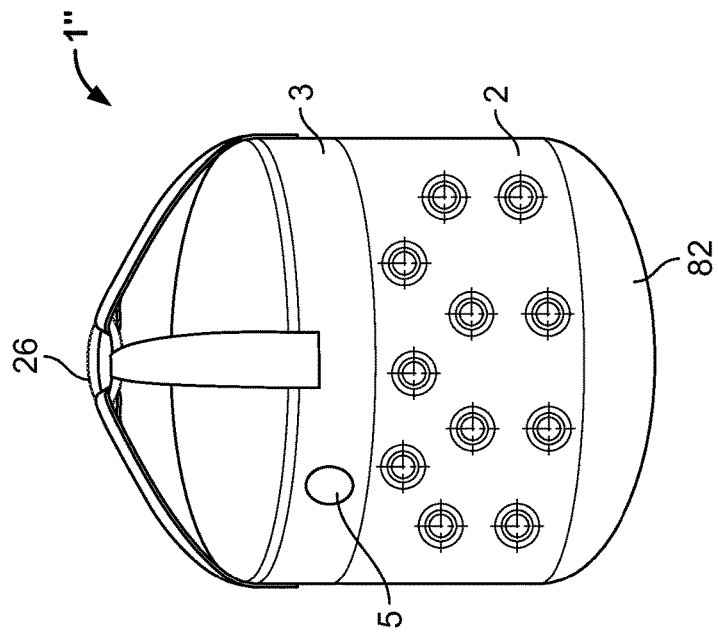
FIGS. 8A and 8B show perspective views of alternative embodiments of the electronic punching bag.
Figure 8B:
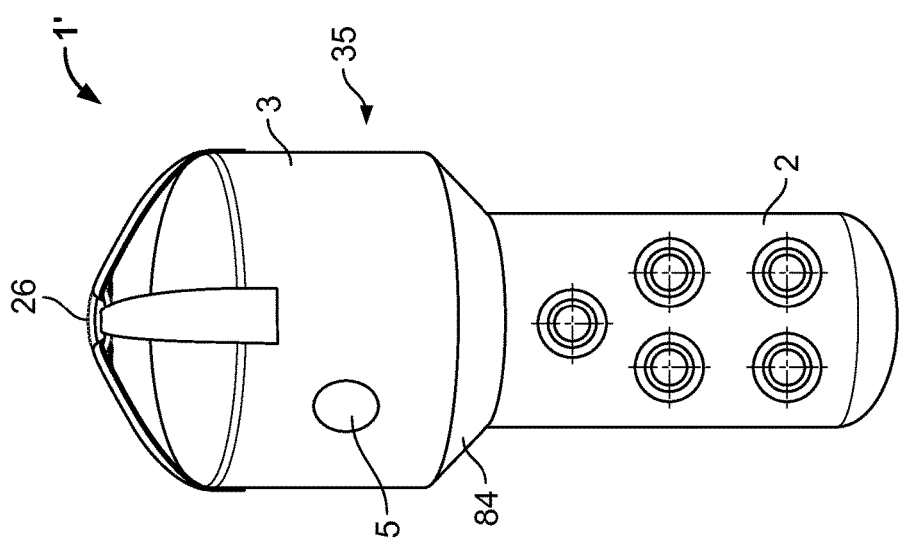

FIG. 7D shows a connecting device 22 connected at the top center of the electronic punching bag 1 and with a single connection accommodation disposed at the top center.

FIGS. 8A and 8B show an embodiment of a connection accommodation 26 that is at single eyelet at the top center of the bag 1' or 1", with four fabric straps extending to the top sides of the bag 1' or 1". The four fabric straps can be sewn or attached into the bag 1' or 1" at the top sides of the bag 1. Alternatively, the connection accommodation could be multiple eyelets dispersed around the top of the bag 1.

The device could also include automatic adjustment features and structure to allow adjustment of the height to better suit a boxer with a different height.

In further embodiments, the electronic punching bag could be supported from the ground instead of being suspended in the air.

With some embodiments, the bag 1 includes an electrical outlet, so that the bag 1 can receive electrical power from a power source such as an AC power input. The electrical outlet can be disposed at a top region of the bag so that an electrical power cord could be plugged into the bag from the top even during a training session without interfering with the training session. The external electrical power cord bringing power to the bag 1 could run with or near the connecting device 22 that suspends the bag 1 in the air above the floor. The electrical outlet could also be disposed at a bottom region of the bag 1 near the display screen and the microprocessor.

The electrical outlet can, for example, be a 110V or 220V AC input.

The bag 1 can include an AC/DC converter to convert AC power to DC power for the main board of the microprocessor and the driver circuits. The bag 1 may also include a DC/DC converter to supply power to various internal components. This second converter converts a DC input power into different levels of DC power as needed by individual components.

The device may alternatively include a chargeable battery system for powering the bag 1 so that the bag 1 does not need to be plugged into an external power source during the training session. The battery could be charged before and after and between training sessions. The battery could in one embodiment entirely replace the electrical outlet.

Figure 9:
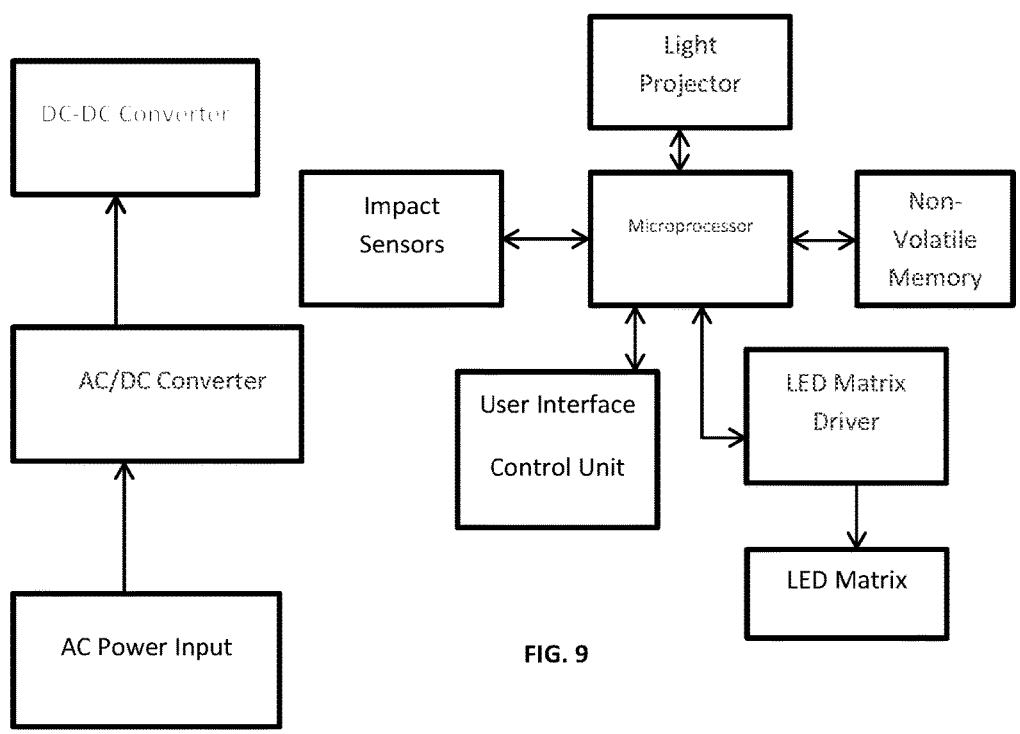
FIGS. 9 and 10 show two different electrical system architecture embodiments for the electronic punching bag.
Figure 10:
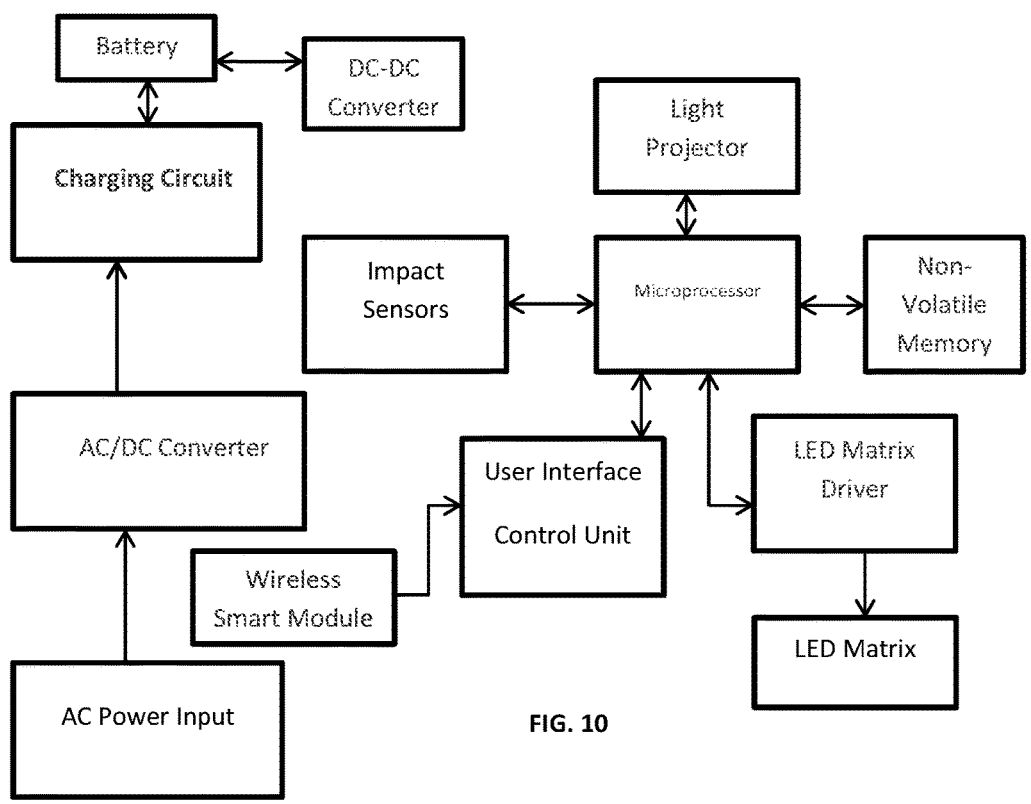

FIGS. 9 and 10 show two different electrical system architecture embodiments for the electronic punching bag 1.

As shown in FIG. 7A, the longitudinal length 31 of the display screen 3 can be at a 1:8 ratio with respect to the longitudinal length 71 of the elongate bag 2. This ratio can be within a range of from 1:3 to 1:10, for example can be 1:4, 1:5, 1:6, 1:7, or 1:9.

Although multiple embodiments of the present invention have been shown and described, it is to be understood that many changes and modifications may be made thereunto without departing from the spirit and scope of the invention as defined in the appended claims.

What is claimed is:

1. An electronic punching bag comprising:
   (a) an elongate bag formed of resilient material;
   (b) a microprocessor disposed in an interior of the electronic punching bag or at a periphery of the electronic punching bag; and
   (c) a display screen extending around more than half of the periphery of the electronic punching bag and configured to receive signals from the microprocessor, the signals causing the display screen to display visual signals, the display screen forming an exterior face of the electronic punching bag.

2. The electronic punching bag according to claim 1, wherein the display screen is an LED matrix display or an LCD panel.

3. The electronic punching bag according to claim 1, further comprising:
   sensors in the elongate bag and
   target symbols disposed as a symbolic matrix forming a brain maze on an exterior of the elongate bag,
   wherein each target symbol of the target symbols is aligned with a respective sensor of the sensors.

4. The electronic punching bag according to claim 1, wherein at least one signal of the signals from the microprocessor to the display screen causes the display screen to display at least one pattern matching at least one target symbol of the elongate bag.

5. The electronic punching bag according to claim 1, further comprising a connection accommodation configured to allow the electronic punching bag to connect with a connecting device so that the electronic punching bag is suspended above the ground.

6. The electronic punching bag according to claim 3, wherein the sensors are connected with the microprocessor to send sensor signals to the microprocessor, and
   wherein the microprocessor comprises memory and is programmed to record and store the sensor signals to track punching performance of a user using the electronic punching bag.

7. The electronic punching bag according to claim 1, wherein the display screen extends around at least eighty percent of the periphery of the elongate bag.

8. The electronic punching bag according to claim 1, further comprising a light configured to emit light downwards and to project a line signal on a surface below the electronic punching bag when the electronic punching bag is suspended in the air above the surface.

9. The electronic punching bag according to claim 8, wherein the light comprises a laser light.

10. The electronic punching bag according to claim 3, wherein the signals from the microprocessor cause the display screen to display a question, and
    wherein a correct answer to the question matches at least one target symbol of the target symbols.

11. The electronic punching bag according to claim 1, wherein the signals from the microprocessor cause the display screen to display symbols representing a boxing training regimen.

12. The electronic punching bag according to claim 11, wherein the training regimen comprises a fight choreography of a past boxing match.

13. The electronic punching bag according to claim 1, further comprising a control unit connected to the microprocessor,
    wherein the control unit is disposed on an exterior of the electronic punching bag and comprises input devices configured to receive input from a user.

14. The electronic punching bag according to claim 1, further comprising a protective cage disposed at a bottom of the electronic punching bag.

15. The electronic punching bag according to claim 14, wherein the protective cage comprises at least one spring.

16. The electronic punching bag according to claim 1, wherein the microprocessor has a wireless connection with the display screen, and
    wherein the microprocessor can send the signals to the display screen via the wireless connection.

17. The electronic punching bag according to claim 1, wherein the microprocessor is configured to receive a wireless signal and to receive instructions via the wireless signal.

18. The electronic punching bag according to claim 1, further comprising an audio speaker having a connection to the microprocessor.

19. An electronic punching bag comprising:
    (a) an elongate bag formed of resilient material;
    (b) a microprocessor disposed in an interior of the electronic punching bag or at a periphery of the electronic punching bag;
    (c) a display screen extending around more than half of the periphery of the electronic punching bag and configured to receive signals from the microprocessor, the signals causing the display screen to display visual signals; and (d) a light disposed at a bottom of the electronic punching bag and configured to emit light downwards and to project a line signal on a surface below the electronic punching bag when the electronic punching bag is suspended in the air above the surface.

20. An electronic punching bag comprising:
(a) an elongate bag formed of resilient material and comprising an outer surface and a plurality of target symbols disposed on the outer surface;
(b) a microprocessor disposed in an interior of the electronic punching bag or at a periphery of the electronic punching bag; and
(c) a display screen extending around more than half of the periphery of the electronic punching bag and configured to receive signals from the microprocessor, the signals causing the display screen to display visual signals,
wherein at least one signal of the signals from the microprocessor to the display screen causes the display screen to display at least one pattern matching at least one of the target symbols of the elongate bag.

* * * * *